United States Patent
Watson et al.

[11] Patent Number: 5,676,672
[45] Date of Patent: Oct. 14, 1997

[54] UMBILICAL CORD CLAMPS WITH SHIELDED CUTTER

[76] Inventors: Thomas J. Watson, 116 Royal Dr., Madison, Ala. 35758; Richard L. Watson, Jr., 823 N. Main, McPherson, Kans. 67460

[21] Appl. No.: 554,316

[22] Filed: Nov. 8, 1995

[51] Int. Cl.$^6$ ............................. A61B 17/42; A61B 17/46
[52] U.S. Cl. .......................................... 606/120; 606/167
[58] Field of Search .................................. 606/120, 157, 606/174, 142, 167

[56] References Cited

U.S. PATENT DOCUMENTS

| | | | |
|---|---|---|---|
| 3,106,919 | 10/1963 | Churchville | 606/120 |
| 3,631,858 | 1/1972 | Ersek | 606/120 |
| 4,572,181 | 2/1986 | Mattler | 128/305 |
| 4,648,401 | 3/1987 | Mattson | 128/305 |
| 4,716,886 | 1/1988 | Schulman et al. | 606/120 |
| 4,781,188 | 11/1988 | Collins | 128/305 |
| 4,856,517 | 8/1989 | Collins et al. | 128/346 |
| 4,938,215 | 7/1990 | Schulman et al. | 606/120 |
| 5,009,657 | 4/1991 | Cotey et al. | 606/120 |
| 5,127,915 | 7/1992 | Mattson | 606/120 |
| 5,178,624 | 1/1993 | Kyun | 606/120 |
| 5,190,556 | 3/1993 | Hessel | 606/120 |
| 5,415,665 | 5/1995 | Hessel et al. | 606/120 |

*Primary Examiner*—Robert A. Hafer
*Assistant Examiner*—Justine Yu

[57] ABSTRACT

A disposable umbilical clamp and cutter (10) for clamping a newly born infants umbilical cord in two places, then cutting the cord in between the two clamps (12,14). The clamps are separated and the infant retains its clamp (14) for a short period of time. The clamping surfaces (22) are formed in symmetrical upper (16) and lower (18) halves that rotate about a fold (20) of joining material. Each pair of halves form an enclosed cylinder around the centered umbilical cord when the clamps are closed. Break away connections (24) between the clamps keep them in a semi-rigid, side-by-side arrangement. The clamps are individually closed by putting pressure on two thumb rests (26,28), and opposing pressure with fingers on the lower halves (18), until latches (44) mate with corresponding latch stops (46). Clamps are clearly marked for use on the baby side (14) or the maternal side (12). A 'V'-shaped blade (30) is located inside a vertical channel (32) in the maternal clamp (12). The maternal thumb rest (28) is flexible and moves at one end to make contact with the top, non-cutting, edge of the blade (30). Pressure on the maternal thumb rest (28) forces the blade (30) out of its inclosed channel (18) and cuts the cord. With proper use, the blade remains shielded from the user and the baby to help insure safe cutting. After the clamps are closed and the cord is severed, the two clamps are separated at the break-away connections (24). Force is applied with hand pressure only at the clamp ends with an opposing force near the break-away connections (24) to separate the clamps.

2 Claims, 3 Drawing Sheets

UMBILICAL CORD CLAMPS WITH SHIELDED CUTTER

BACKGROUND

1. Field of Invention

This invention relates to disposable surgical clamps, specifically those which clamp and cut a baby's umbilical cord at birth.

2. Description of Prior Art

It is common practice in a hospital delivery room to use two separate clamps on the umbilical cord, and then cut the cord with scissors or a scalpel. One clamp remains with the baby until the blood clots and the piece of cord drops off at the baby's navel. The other clamp is disposed of with the placenta. The clamp that remains with the baby is placed about 5 to 8 cm from the baby's abdomen. Because of the clamp's proximity to the baby, and to prevent possible transmission of a disease such as hepatitis and/or AIDS, a safer method is desired. Also, since this procedure is performed directly after the baby is delivered, a quick and easy method is desired to allow more time for other critical procedures.

Inventors have created several new devices to clamp and cut the umbilical cord in an efficient manner. These new types can be placed into the following categories: simple stacked type, scissors type, plunger type and blood collecting type.

The simple stacked types use dual clamps that are stacked side by side, but are separable. The clamps move in unison and are installed much as a single clamp would be installed. A cutting blade is attached to the maternal clamp to cut the cord with clamping action. An early example of this type is shown in U.S. Pat. No. 3,631,858 to Ersek (1972). This proposed device is composed of a minimum of 6 parts and does not provide protection from the cutting edge of the blade to the user or baby. When the clamps are open, the blade edge is exposed between the clamps, and accidental injury could occur. When separating the clamps a hazard still exists from the partially exposed blade edge. An improvement on this basic design is shown is U.S. Pat. No. 4,938,215 to Schulman et al. (1990). This device clamps first, then cuts with continued applied pressure. When the umbilical cord is cut, shear pins are then cut which separate the two clamps. This device requires a minimum of 5 separate pieces to be manufactured, and also does not provide protection from the cutting edge of the blade. These devices can be put on backwards by mistake, because the side by side clamps look very similar and no marking for correct use is indicated. This could result in injury to the baby, because the exposed blade could mistakenly be attached to the clamp on the baby's side. Furthermore, these clamps are relatively long when compared with discrete clamps. They do not provide any strain relief to the umbilical cord against forces on clamp ends after the clamp is installed. This could result in tearing of the cord and hemorrhaging. The simple stacked types are also prone to slippage during use. Good leverage is hard to obtain against their flat handling surfaces, especially when gloved hands are wet.

The scissors types look like scissors and also have dual clamping capability. They have a cutter that works just prior to complete clamping when the scissors are closed. A good example of this type is shown in U.S. Pat. No. 5,127,915 to Mattson (1992). The clamp put on the baby's side is released from the scissors' jaws after the clamp is closed. The scissors portion would require sterilization and another clamp to be loaded for reuse. This device requires a minimum of 5 separate pieces to be manufactured and assembled, and does not provide protection from the cutting edge of the blade. This type of device could also be used backwards and cause injury, and does not provide a clear visual indication for proper orientation.

The plunger type introduced in U.S. Pat. No. 4,572,181 to Mattler (1986) is one of the most complicated of these types of devices. It has two blades in a 'V' shape at the end of a plunger that is assembled into a clamp carrier. The plunger acts to compress two clamps closed and cut the umbilical cord. At the end of the plunger stroke, the two clamps are pushed away from the clamp carrier and the operation is complete. This device requires setup time to install the plunger and clamps prior to use. The plunger and carrier could be reused, but would require sterilization and repeated setup. This device was designed to cover a wider range of applications than the clamp described herein. For example, the size of this device is small, allowing it to be used like a syringe in other procedures where space is limited. This plunger style requires a minimum of 10 separate parts to be manufactured. It does solve the problem of shielding the cutting blades, but requires tedious assembly and has high manufacturing costs.

The blood collecting type introduced in U.S. Pat. No. 5,190,556 to Hessel (1993) and continued in U.S. Pat. No. 5,415,665 to Hessel et al. (1995) is another example of a complicated device. The design has a side by side, hinged, simultaneous clamping action like that of the simple stacked types. This design uses a sealed arrangement and has provisions for connecting vacuum tubes for automatic blood collection when the cord is severed. The blade is shielded and held in place with a safety catch. Pressing the safety catch allows the blade to slide, cut the cord and eject the babies clamp. This style requires a minimum of 24 separate parts to be manufactured. It does solve the problem of shielding the cutting blades, but requires tedious assembly and has high manufacturing costs.

These four types of clamping and cutting devices make the task of clamping and severing the umbilical cord easier. This is done by combining tasks, previously taking separate actions, into one user action. While the task is made more convenient, only the plunger and blood collecting types address shielding the cutting blades for user and baby safety. The simplest types are prone to slippage, especially when the user's gloves are wet. All of these foregoing types require 5 or more parts in their assemblies, and the plunger and blood collecting types which provide safety from the blade require 10 or more parts. Their designs are considered overly complicated and have high manufacturing costs.

OBJECTS AND ADVANTAGES

Accordingly, several objects and advantages of the present invention are:

(a) to provide umbilical clamps with cutter which are convenient to install and provide shielding of the blade to protect the baby and the user.

(b) to provide an easily manufactured clamp, using injection molding and requiring only one additional part (the blade) to make up the assembly.

(c) to provide clamps of minimum size when installed, especially for the baby clamp, and still be large enough for easy handling.

(d) to provide end guides that help align the clamp during installation and also provide strain relief, to help prevent cord tearing at the clamp on the baby's side.

(e) to provide thumb rests and a holding ring to aid in leverage in closing the clamps.

(f) to provide color-coded identification to differentiate between maternal and baby clamps to help prevent installing the device backwards.

(g) to provide clamps with small break-away connections to allow easy two handed separation without any tool or instrument.

Still further objects and advantages will become apparent from a consideration of the ensuing description and drawings.

DRAWING FIGURES

Figure 1:
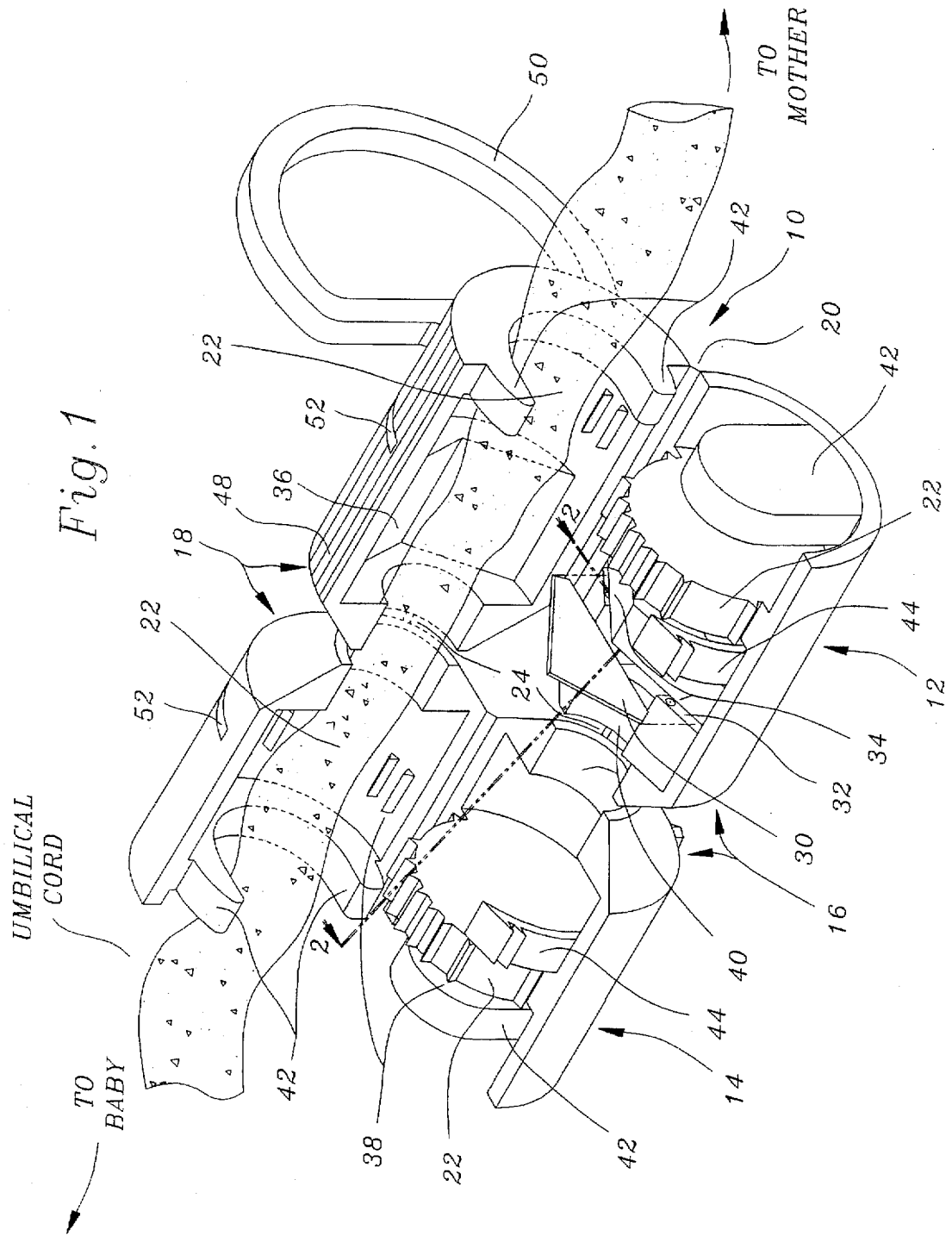
FIG. 1 is an exploded, perspective view of a umbilical cord clamps with shielded cutter in accordance with the present invention.
Figure 2:
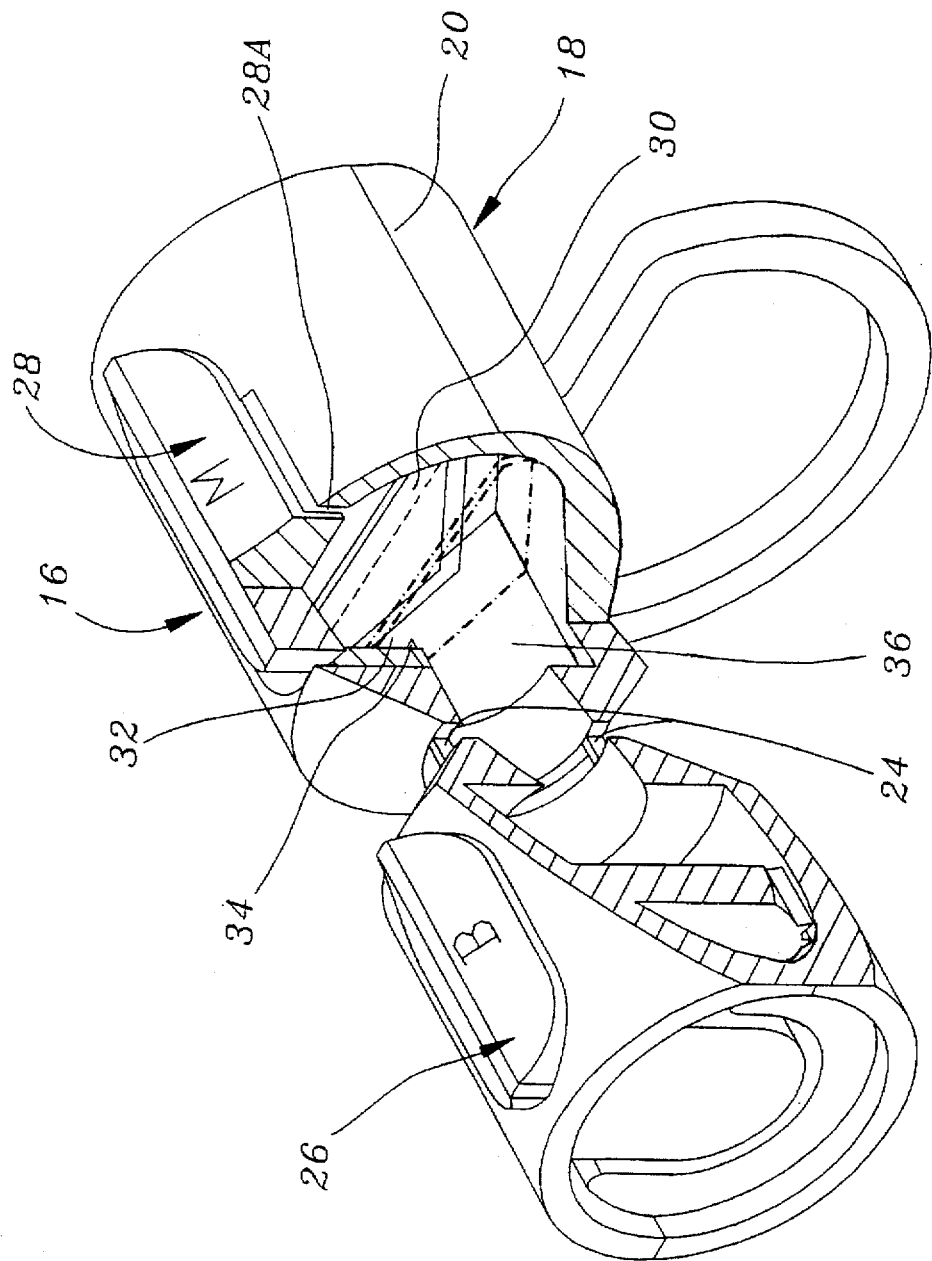
FIG. 2 is a cross sectional view taken across 2—2, in FIG. 1 illustrating the blade movement to severe the umbilical cord.
Figure 3:
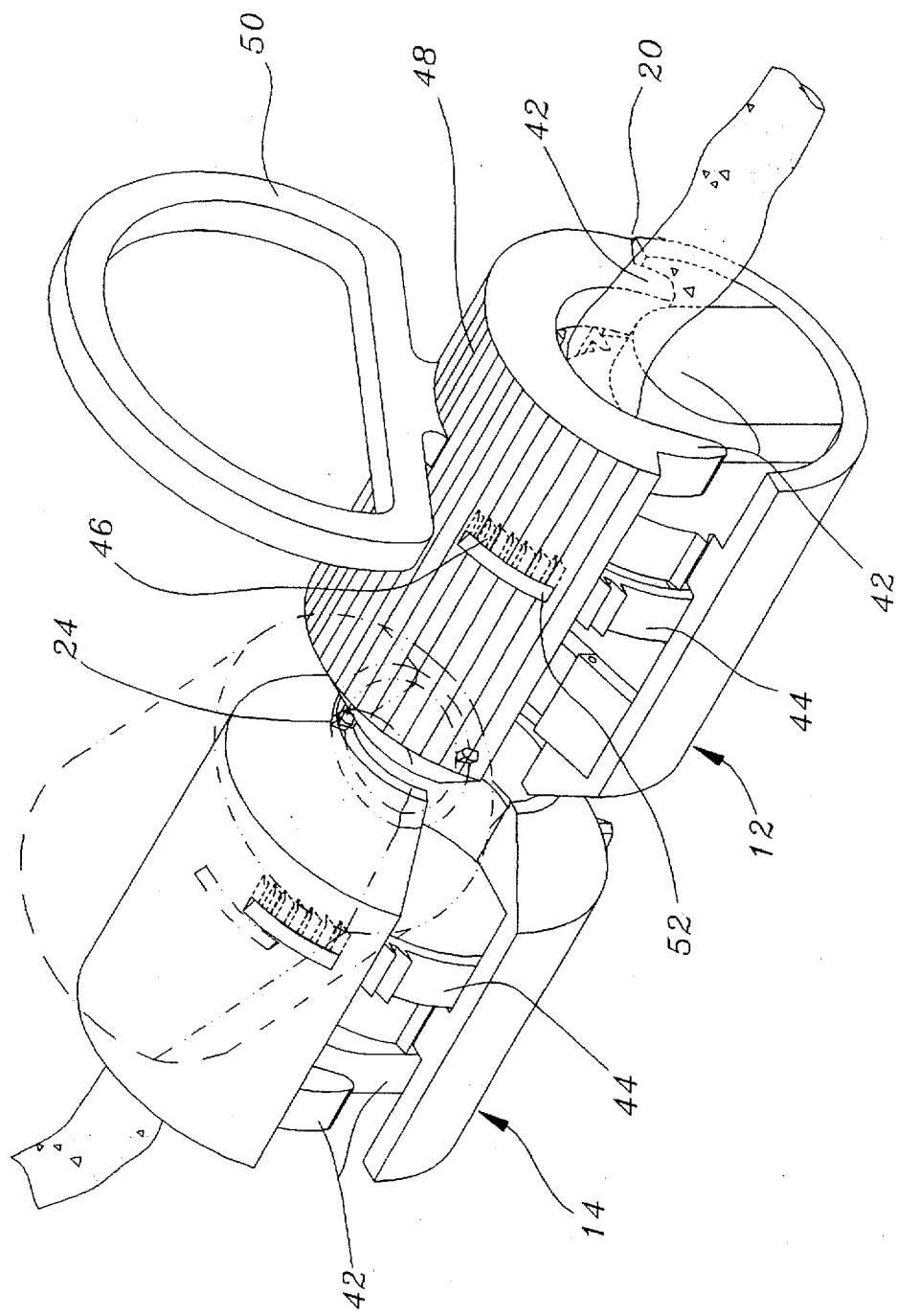
FIG. 3 is an exploded, perspective view with clamps going to the closed position, and illustrating separation of the two clamps.

DESCRIPTION-FIGS. 1 to 3

A typical embodiment of the clamp of present invention is illustrated in FIG. 1. The clamp 10 has two pairs of clamp sections, each pair forming a clamp. One is designated with a 'B' for baby clamp 14 and the other with an 'M' for maternal clamp 12 (see FIG. 2). Each pair of upper 16 and lower halves 18 are joined lengthwise by a bendable fold 20 to allow repeated closure of each clamp. A blade channel 32 is formed in the maternal clamp 12 and has two blade rests 34 to contain the blade before cutting pressure is applied. The two blade rests 34 are conical protrusions extending into the blade channel 32 which keep the blade 30 from falling out due to the force of gravity. The blade rests 34 are made such that they will deform with pressure applied allowing the blade 30 to be inserted or removed from the blade channel 32. When the blade 30 is inserted into the blade channel 32, the cutting edge is recessed within the channel to help shield the cutting edge from human touch.

The baby clamp 14 and maternal clamp 12 are joined together with two small sections of material called breakaway connections 24 that will allow easy separation after clamps are closed and the umbilical cord has been cut. The entire part except for the blade 30 can be injection molded at one time. The material used is a flexible plastic not limited to but including olefin resins, such as used in other disposable medical products. The preferred color of the material, excluding thumb rests, is clear or transparent. The thumb rest 26 and 28 colors are preferably blue and red, but any other easily differentiated colors can be used at the baby and maternal thumb rests, respectively.

The size and shape of the baby clamp 14 is important, since it remains with the baby for some time after being attached at birth. Minimizing this size is important while still allowing the operator to easily handle and close the clamp. The clamping surfaces 22 must also be long enough with proper separation to displace the cord and clamp properly for all sizes of babies' cords. For these reasons, the clamping surface 22 is curved about the inside of the clamp enclosure. The clamping surface 22 is approximately 25 mm long with a closed clamp separation of 2 mm. The clamping surfaces have teeth 38 which are alternately spaced between upper and lower halves to provide more complete clamping action. Cord guides 40 are provided to center the cord for clamping. They form a hole that is about the same size as the umbilical cord. Cord guides 40 have a radius of approximately 7 mm. The overall diameter of the baby clamp 14 when closed is 21 mm. The external diameter of the maternal clamp 12 is the same size to provide uniform handling and feel to the operator's hands. The thumb rest, baby side 26 and the thumb rest, maternal side 28 are raised and shaped to provide good leverage for clamp closure. Additional leverage is provide by a holding ring 50 on the maternal clamp 12 lower half 18. The plane of the holding ring 50 is parallel to the plane bisecting clamping surfaces 22. The ring 50 is sized for one, finger, partially inserted. Also improving leverage is an anti-skid surface 48 on the maternal clamp 12 lower half 18.

The maternal side thumb rest 28 is depicted in FIG. 2. It is cut away on the inside and has a blade actuator 28A beneath the cutaway end. This thumb rest will bend, forcing the blade 30 to press against blade rests 34, and deform them forcing the blade 30 out of the blade channel 32 to cut the cord after clamping. The blade stop 36 provides a surface to cut against and matches the shape of the cutting edge.

FIG. 3 shows the two clamps closed and separated. The clamps stay closed due to a latch 44 on each clamp upper half 16 that mates with an adjustable latch stop 46 on the lower half 18. The latch bends with applied pressure forcing the two halves together and catches on the stops 46 to keep the clamp in a closed position. Each latch stop 46 has a series of catches to provide adjustable clamp separation and pressure. Release holes 52 adjacent to the latch stops allow release of the latch using a pointed instrument. Strain relief of the umbilical cord is provided by the end guides 42. These guides limit the distance the cord can bend near the clamp and tend to keep the clamp and cord perpendicular to one another.

OPERATION-FIGS. 1 to 3

This device is operated in a two-handed manner. One hand in used to grasp one of the clamps, preferably the maternal clamp 12 first. Since the maternal clamp 12 is the largest in size and has a holding ring 50 and non-skid surface 48 on the lower half 18, it will be the easiest to handle. The user's thumb is placed on the thumb rest, maternal side 28, and one finger is placed into the holding ring 50. Other fingers may rest on the lower half 18. At this point, the clamp is positioned so the umbilical cord rests on the lower portion of both clamps in the cord guides 40 and end guides 42. The clamp is partially closed as shown in FIG. 1. The end of the baby clamp is oriented so there is only 5–8 cm of cord length between the baby's abdomen and the clamp. The maternal clamp 12 is on the side connected to the placenta. The free hand can be used to help position the umbilical cord with respect to the baby clamp 14. The two clamps will not stay exactly inline with the longitudinal axis, because of bending at the break-away connections 24. Support by fingers of the hand holding the maternal clamp 12 can be used under the baby clamp 14 to eliminate this problem. At this point, the maternal clamp 12 can be closed. Note that clamping pressure on the maternal clamp thumb rest 28 should be placed near the end of the clamp away from the blade actuator 28A. The other hand can now be used to hold the baby clamp 14. This clamp can be closed by pressing with the thumb on the thumb rest 26 and fingers on the lower half 18 in a similar manner as the maternal clamp 12.

At this point, both clamps should be closed and the latches 44 should be mated with their respective latch stops 46. The next step is to severe the cord. This is accomplished by applying force to the maternal side thumb rest 28 at the inside end where the actuator 28A is connected (see FIG. 2). The blade 30 will cut through the cord and hit the blade stop 36. The final step is to break apart the two clamps. FIG. 3 shows the clamps before and after separation. Separation is accomplished by placing pressure at the ends with either the fingers or thumbs and opposing pressure near the break-away connections 24 with remaining fingers or thumbs. If thumbs are used at the ends, then fingers are used near the break-away connections 24 and vice versa for an alternate method. Two connections must be broken and care should be taken to not put stress on the cord portion leading to the baby. Scissors or a scalpel can be used to cut the connections 24 as an alternate method of separating the two clamps. Either clamp can be removed by inserting a small, pointed object like a pen into the release hole 52, pressing against the latch 44, while applying pressure to separate the halves.

SUMMARY, RAMIFICATIONS, AND SCOPE

Accordingly, the reader will see that the umbilical cord clamps with cutter of the present invention can be used to conveniently clamp and sever babies' umbilical cords. Umbilical cord guides, a holding ring, and thumb rests help provide easy installation. The size of the baby clamp is minimized and designed to provide strain relief. Break-away connections provide a way of separating the clamps by hand, without the use of instruments.

In addition, the clamp helps to protect the baby and the user from the cutting blade by shielding it before, during, and after its use. It uses colored identification and letter markings on the two clamps to provide for correct orientation. For example, the blue side marked 'B' always goes on the baby's side.

The clamp is also inexpensive to manufacture using injection molding and is easily assembled by installing one other part—the blade.

Although the description above contains many specificities, these should not be construed as limiting the scope of the invention, but merely providing illustrations of some of the presently preferred embodiments of this invention. For example, the two clamps could be formed into other shapes such as rectangular, oval, etc.; the anti-skid surface could be checked or of another texture. Thus the scope of the invention should be determined by the appended claims and their legal equivalents, rather than by the examples given.

I claim:
1. A device for clamping and cutting a baby's umbilical cord, said device comprising:
   (a) two clamps in a side-by-side connection, each of said clamps formed substantially symmetrical external clamp enclosures and comprising two curved opposing internal clamping surfaces, one of said curved clamping surfaces comprising a hinged connecting means and the other one of said curved clamping surfaces comprising a latching means for locking the symmetrical clamp enclosures together;
   (b) a breakable connecting means for maintaining said side-by-side connection between said clamp enclosures; and
   (c) equally spaced openings in ends of said clamp enclosures having means adapted to center the umbilical cord; and
   (d) a thumb rest on each said clamp enclosure comprised of raised material of contoured shape, each of said thumb rest containing different letter and color markings indicating clamp orientation, one side for baby and one indicating maternal side; and
   (e) a holding ring attached to one of said clamp enclosures, designated as the maternal side, on a half opposite said thumb rest for user to insert a finger and support said device longitudinally; and
   (f) one of said thumb rests, designated as maternal side, having flexible means to bend with applied pressure, and
   (g) a cutting blade releasably contained in a channel in the maternal side clamp enclosure, said cutting blade in contact with the bendable maternal side thumb rest, said cutting blade having means to move with pressure applied to the bendable thumb rest to severe the cord, whereby said device is applied to an umbilical cord, said clamps individually or simultaneously latched, and then pressure applied to the maternal side thumb rest to release the blade from its shielded position within said channel and cut the cord, and then said clamp enclosures separated and left in place on the cut ends of the cord.

2. The device of claim 1 wherein said device can be made using a single molding process.

* * * * *